US007332227B2

(12) United States Patent
Hardman et al.

(10) Patent No.: US 7,332,227 B2
(45) Date of Patent: Feb. 19, 2008

(54) NON-VOLATILE LUBRICANT SYSTEM FOR MEDICAL DEVICES

(75) Inventors: Lori Hardman, Lebanon, NH (US); Mark Spinti, Sandy, UT (US); Jie Jane Ren, Warren, NJ (US); An-Min Jason Sung, Warren, NJ (US); Brian James Pelkey, Rockaway, NJ (US); Shang-Ren Wu, Mahwah, NJ (US); Lawrence Korona, West Paterson, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 498 days.

(21) Appl. No.: 10/792,990

(22) Filed: Mar. 4, 2004

(65) Prior Publication Data

US 2004/0209784 A1 Oct. 21, 2004

Related U.S. Application Data

(60) Provisional application No. 60/454,735, filed on Mar. 14, 2003.

(51) Int. Cl.
*C08K 5/5419* (2006.01)
(52) U.S. Cl. .................. 428/447; 522/99; 522/148; 526/279; 524/731
(58) Field of Classification Search .............. 428/447; 522/99, 148; 526/279; 524/731
See application file for complete search history.

(56) References Cited

U.S. PATENT DOCUMENTS

| | | | |
|---|---|---|---|
| 3,574,673 A | 4/1971 | Schwelger | 117/132 |
| 4,488,986 A | 12/1984 | Naarmann et al. | 428/447 |
| 4,534,363 A | 8/1985 | Gold | 128/772 |
| 4,582,762 A | 4/1986 | Onohara et al. | 428/447 |
| 4,596,720 A * | 6/1986 | Keryk et al. | 427/503 |
| 4,664,657 A | 5/1987 | Williamitis et al. | 604/265 |
| 4,686,124 A | 8/1987 | Onohara et al. | 428/35 |
| 4,720,521 A | 1/1988 | Spielvogel et al. | 524/862 |
| 4,806,430 A | 2/1989 | Spielvogel et al. | 428/450 |
| 4,814,231 A | 3/1989 | Onohara et al. | 428/425 |
| 4,838,876 A | 6/1989 | Wong et al. | 604/265 |
| 4,904,433 A | 2/1990 | Williamitis | 264/130 |
| 4,987,169 A | 1/1991 | Kuwata et al. | 524/267 |
| 5,013,717 A | 5/1991 | Solomon et al. | 514/56 |
| 5,026,607 A | 6/1991 | Kiezulas | 428/423 |
| 5,055,229 A | 10/1991 | Pelton et al. | 252/321 |
| 5,061,738 A | 10/1991 | Solomon et al. | 523/100 |
| 5,084,315 A | 1/1992 | Karimi et al. | 428/36.6 |
| 5,185,006 A | 2/1993 | Williamitis et al. | 604/265 |
| 5,186,972 A | 2/1993 | Williams et al. | 427/2 |
| 5,258,013 A | 11/1993 | Granger et al. | 606/223 |
| 5,266,359 A | 11/1993 | Spielvogel | 427/388.4 |
| 5,338,770 A | 8/1994 | Winters et al. | 523/112 |
| 5,456,948 A | 10/1995 | Mathisen et al. | 427/387 |
| 5,458,616 A | 10/1995 | Granger et al. | 606/223 |
| 5,536,582 A | 7/1996 | Prasad et al. | 428/450 |
| 5,653,695 A | 8/1997 | Hopkins et al. | 604/256 |
| 5,670,558 A | 9/1997 | Onishi et al. | 523/112 |
| 5,688,747 A | 11/1997 | Khan et al. | 508/208 |
| 5,712,229 A | 1/1998 | Hopkins et al. | 508/202 |
| 5,712,391 A | 1/1998 | Ohno et al. | 544/194 |
| 5,736,521 A | 4/1998 | Bylund et al. | 428/447 |
| 5,824,359 A | 10/1998 | Khan et al. | 427/2.3 |
| 5,859,243 A | 1/1999 | Ohno et al. | 544/229 |
| 5,908,686 A * | 6/1999 | Sudo et al. | 428/215 |
| 5,911,711 A | 6/1999 | Pelkey | 604/265 |
| 6,015,398 A | 1/2000 | Arimatsu et al. | 604/272 |
| 6,046,143 A | 4/2000 | Khan et al. | 508/208 |
| 6,066,602 A | 5/2000 | Khan et al. | 508/436 |
| 6,086,970 A | 7/2000 | Ren | 428/36.9 |
| 6,102,898 A | 8/2000 | Khan et al. | 604/265 |
| 6,106,889 A | 8/2000 | Beavers et al. | 427/2.1 |
| 6,113,567 A | 9/2000 | Becker | 604/8 |
| 6,117,480 A | 9/2000 | Spallek et al. | 427/2.3 |
| 6,165,158 A | 12/2000 | Dutta | 604/265 |
| 6,176,849 B1 | 1/2001 | Yang et al. | 604/265 |
| 6,221,061 B1 | 4/2001 | Engelson et al. | 604/265 |
| 6,261,630 B1 | 7/2001 | Nazarova et al. | 427/2.12 |
| 6,291,563 B1 | 9/2001 | Horne et al. | 524/267 |
| 6,331,329 B1 | 12/2001 | McCarthy et al. | 427/387 |
| 6,406,792 B1 | 6/2002 | Briquet et al. | 428/447 |
| 6,669,980 B2 | 12/2003 | Hansen | 427/2.24 |
| 6,673,053 B2 | 1/2004 | Wang et al. | 604/265 |
| 6,673,385 B1 | 1/2004 | Ding et al. | 427/2.38 |
| 6,673,458 B2 | 1/2004 | Mager et al. | 428/450 |
| 6,673,459 B2 | 1/2004 | McCarthy et al. | 428/450 |
| 2003/0054090 A1 | 3/2003 | Hansen | 427/2.1 |
| 2003/0096131 A1 | 5/2003 | Beavers et al. | 428/522 |
| 2003/0104227 A1 | 6/2003 | McCarthy et al. | 428/450 |
| 2003/0236552 A1 | 12/2003 | Roby | 606/223 |
| 2005/0203201 A1* | 9/2005 | Steube | 522/15 |

FOREIGN PATENT DOCUMENTS

JP 178159 7/1995

* cited by examiner

*Primary Examiner*—Margaret G. Moore
(74) *Attorney, Agent, or Firm*—Mark Lindsey

(57) ABSTRACT

A non-volatile lubricious coating composition is provided for use with medical devices, such as hypodermic needles, catheters, and the like. The coating composition includes a first siloxane polymer having a very low viscosity less than about 50 centistokes, a second siloxane polymer having a high viscosity greater than about 1,000 centistokes, a reactive silicone polymer which is capable of crosslinking upon exposure to radiation, such as a UV curable silicone acrylate, and a photoinitiator to accelerate cross-linking of the reactive silicone polymer. The coating composition may further include an aminofunctional siloxane polymer to promote adhesion to metal surfaces when used with needles. The coating composition provides flowability without the need for any volatile organic solvent, and is capable of curing to provide adhesion and lubricity.

43 Claims, No Drawings

NON-VOLATILE LUBRICANT SYSTEM FOR MEDICAL DEVICES

CROSS REFERENCE TO RELATED APPLICATION

The present application claims the benefit of U.S. Provisional Application No. 60/454,735 filed Mar. 14, 2003 entitled "Non-Volatile Lubricant System for Medical Devices", incorporated herein by reference.

BACKGROUND OF THE INVENTION

1. Field of Invention

The present invention is directed to a lubricant system for medical devices. More particularly, the present invention is directed to a non-volatile lubricious coating for hypodermic needles, catheters, and the like.

2. Description of Related Art

It has become commonplace in the medical field to provide medical devices with lubricants for ease of use. For example, hypodermic needles are widely used in delivering and withdrawing fluids in medical practice. As originally used, hypodermic needles were used many times, the needles being sterilized between usages. A practitioner would sharpen the needles when they became dull, and then sterilize them prior to the next usage. Since the needles were reused, and often may have needed sharpening, the presence or absence of any lubrication on the outer surface of the needle had little effect on the penetration force or the pain perceived by the patient who was the recipient of the needle. With the development of commercially manufactured disposable needles that always have a fresh well-sharpened point, there was recognition that lubrication of the needle substantially reduced the pain perceived by the patient when a needle was administered to them.

A convention is followed in this disclosure wherein the portion of a device toward the practitioner is termed proximal and the portion of the device toward the patient is termed distal.

A tissue penetration by a hypodermic needle involves a sequence of events that collectively are perceived by the patient as whether or not the penetration causes pain. A distal point of the needle first touches the skin surface, stretches it, the point then cuts into the surface and begins penetration into the tissue. As the shaft of the needle passes through the original cut and into the tissue, there is also sliding friction of the tissue against the needle surface. In the hypodermic needle art when the forces for performing a hypodermic needle penetration are measured, the force measured prior to the needle point cutting the tissue is termed the "peak penetration force", also called "F2" and the force required to continue the penetration into the tissue is called the "drag force" or "F4". One primary component of the drag force is the sliding friction of the tissue against the surface of the needle shaft.

Insertion of intravenous (IV) catheters into a patient causes similar issues regarding ease of insertion and patient discomfort. For example, IV catheters are designed to infuse normal intravenous solutions, including antibiotics and other drugs, into a patient. These catheters are also used to withdraw blood from the patient for normal blood-gas analysis as well as other blood work. The most common type of IV catheter is an "over the needle" catheter, in which a catheter is disposed over an introducer needle or cannula, which is used to insert the IV catheter into a patient. The needle is typically stainless steel and is hollow. Its distal tip is ground to a sharp tip for easy insertion into the patient. The catheter is also hollow and is disposed such that the sharpened tip of the needle is extended from the catheter for piercing of the patient's skin during use. Once the skin and vein have been pierced, the catheter is advanced over the needle and the needle is removed from the catheter. The catheter is typically extruded out of suitable plastic material such as TEFLON material (polytetrafluoroethylene), polyvinyl chloride, polyethylene, polyurethane or polyether urethane.

The use of lubricants on the surface of such hypodermic needles and IV catheters significantly reduces both the peak penetration force and the drag force. As a result, almost all single-use sterile disposable needles and IV catheters are supplied with a lubricant already applied to substantially the entire outside surface. A number of lubricants have been developed for use in such applications. Typically, such lubricants involve a medical grade polydimethylsiloxane which is commonly applied to the surface through a volatile carrier solvent which rapidly evaporates. For example, U.S. Pat. No. 5,911,711 to Pelkey discloses a lubricant system for hypodermic needles which includes a first layer formed from an at least partially cured organosiloxane copolymer and a polydimethylsiloxane that has a viscosity greater than about 1000 centistokes, and a second layer over the first layer that includes a polydimethylsiloxane having a viscosity of 50-350 centistokes. The coating compositions of the first and second layers are applied through a volatile carrier solvent such as a chlorofluorocarbon (CFC), and the first layer is thermally cured by applying heat. Unfortunately, volatile solvents such as CFC's raise significant environmental concerns.

There is a need in the medical industry for lubricants for medical devices such as catheters and needles which are environmentally friendly, which are easy to apply, and which do not involve the use of volatile organic solvents such as CFC's.

SUMMARY OF THE INVENTION

The present invention is directed to a film-forming composition including a first siloxane polymer having a viscosity of less than about 50 centistokes, a second siloxane polymer having a viscosity of greater than about 1,000 centistokes and desirably greater than about 5,000 centistokes, a reactive silicone polymer capable of crosslinking upon exposure to radiation, and a photoinitiator for accelerating crosslinking of the reactive silicone polymer upon exposure to radiation. The first and second siloxane polymers are desirably polydimethylsiloxanes. The reactive silicone polymer is desirably a silicone acrylate which is capable of crosslinking upon exposure to ultraviolet light in the presence of a photo initiator.

The first siloxane polymer has a very low viscosity, i.e. less than about 50 centistokes and desirably between about 2 and 10 centistokes, and therefore acts as a solvent for the film-forming composition, effectively delivering the composition to a substrate surface without the need for volatile organic solvents. In addition, the first low viscosity siloxane polymer, when combined with the second high viscosity polymer, provides lubricity to the composition.

The film-forming composition is particularly useful for providing a lubricious coating to polymeric substrates including medical devices such as catheters, and to hypodermic needles. The composition may further include a third siloxane polymer having amino functionality, such as an aminopropyl dimethylsiloxane copolymer, which is particularly useful as an adhesion promoter when the composition is used as a lubricious coating for metallic surfaces such as stainless steel needles.

In a further embodiment, the present invention is directed to a medical device with a lubricious coating. The lubricious coating is a reaction product of a first siloxane polymer having a viscosity of less than about 50 centistokes, a second siloxane polymer having a viscosity of greater than about 1,000 centistokes and desirably greater than about 5,000 centistokes, a reactive silicone polymer capable of crosslinking upon exposure to radiation, and a photoinitiator for accelerating crosslinking of the reactive silicone polymer. The medical device may be a polymeric material, such as a catheter. Alternatively, the medical device may be a metallic material, such as a stainless steel needle cannula, in which case the lubricious coating desirably further includes a third siloxane polymer having amino functionality.

In yet a further embodiment, the present invention relates to a method for providing the surface of a medical device with a lubricious coating. In the method, the medical device is contacted with a liquid composition which is substantially free of volatile organic solvent, in particular the film-forming composition noted above. The thus-coated surface is then exposed to radiation, such as UV light, to promote curing of the composition.

Still, in a further embodiment, the present invention relates to a lubricious coating formed as the reaction product of a composition comprising a first siloxane polymer having a viscosity of less than about 50 centistokes, a second siloxane polymer having a viscosity of greater than about 1,000 centistokes, a reactive silicone polymer, and a photoinitiator. The coating is formed from at least partial curing of the composition by exposure to a source of radiation for a sufficient time period to promote crosslinking of the reactive silicone polymer to form a three-dimensional network structure in which at least a portion of the first siloxane polymer and/or the second siloxane polymer is contained.

DETAILED DESCRIPTION OF THE INVENTION

The present invention is directed to a film forming composition which is particularly useful as a lubricious coating for medical devices. The composition includes a mixture of different siloxane components having different viscosities and different reactivities, which provides a coating composition which is capable of being delivered to a substrate without the need for a volatile organic carrier solvent, and which is capable of curing in order to form a lubricious film on the substrate.

Generally, the composition of the present invention includes a mixture of a high viscosity linear siloxane polymer with a reactive silicone polymer, which mixture is dissolved or diluted in a low viscosity siloxane polymer which acts as a carrier for the composition. In particular, the composition includes a first low viscosity siloxane polymer having a viscosity of less than about 50 centistokes, a second high viscosity siloxane polymer having a viscosity of greater than about 1,000 centistokes and desirably greater than about 5,000 centistokes, and a reactive silicone polymer which is capable of crosslinking to form a crosslinked polymer network. As will be discussed in more detail herein, in the presence of the photoinitiator, the reactive silicone polymer cures upon exposure to radiation such as UV light to form a crosslinked three-dimensional network which adheres to the surface of the substrate. At least a portion of the high viscosity linear siloxane polymer and the low viscosity siloxane polymer are contained within the crosslinked network structure as mobile liquid silicone oil and can readily migrate to the surface of the coating, thereby creating a continuously lubricious surface.

The specific viscosities of the various silicone components must be tailored such that the viscosity of the overall composition including each of the components is sufficiently fluid so as to wet out and form an even layer on the substrate surface without the need for any traditional volatile organic solvent. It has been discovered through the present invention that combining siloxanes within specific viscosity ranges provides appropriate film-forming compositions that are capable of sufficiently wetting out on a substrate surface without the need for any traditional inert carriers such as volatile organic solvents. This is in part due to the low viscosity siloxane polymer acting as a carrier for the composition. Moreover, by incorporating curable polymers into the composition, the composition can be at least partially cured after application to a substrate to create a lubricious film which adheres to itself and does not flow, and which is capable of adhering to a substrate surface.

For purposes of the present invention, the term "partially cured" refers to a crosslinked or partially crosslinked polymer or copolymer which has insoluble and infusible coherent three-dimensional structure within which an uncured or partially cured polymer can be contained, and which is capable of adhering to itself and does not readily flow.

A first component of the composition is a low viscosity siloxane polymer which has a viscosity of less than about 100 centistokes, in particular less than about 50 centistokes, desirably less than about 20 centistokes, more desirably from about 2 to about 10 centistokes. The low viscosity siloxane polymer desirably has a number average molecular weight of from about 400 to about 4000, more desirably from about 400 to about 1300. The low viscosity siloxane polymer is in fluid form at room temperature, and is capable of diluting or dissolving other siloxane polymers, as will be discussed in more detail herein.

A second component of the composition is a high viscosity siloxane polymer which has a viscosity greater than about 1,000 centistokes, more desirably greater than about 5,000 centistokes such as from about 5,000 to about 50,000 centistokes, more desirably from about 10,000 to about 15,000 centistokes. The high viscosity siloxane polymer desirably has a number average molecular weight of from about 20,000 to about 150,000, desirably from about 60,000 to about 70,000.

Desirably, the low viscosity siloxane polymer and the high viscosity siloxane polymer are individual polyorganosiloxanes independently selected from compounds defined by the following structure:

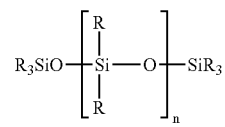

wherein R is selected from the group consisting of $C_{1-20}$ alkyl, haloalkyl, aryl, haloaryl, cycloalkyl, aralkyl, and mixtures thereof, and n is an integer from about 3 to about 1500. Desirably, the low viscosity siloxane polymer is defined by the above structure where n is an integer from about 3 to about 50, and the high viscosity siloxane polymer is defined by the above structure where n is an integer from about 350 to about 1500.

Desirably, both the low viscosity siloxane polymer and the high viscosity siloxane polymer are polydimethylsiloxanes, more desirably trimethylsiloxy-terminated polydimethylsiloxanes.

Non-limiting examples of siloxanes useful as the low viscosity siloxane polymer include PS038 polydimethylsiloxane commercially available from United Chemical Technologies, Inc. of Bristol, Pa., and DMS-T05 polydimethylsiloxane commercially available from Gelest Inc. of Morrisville, Pa., both of which have a viscosity of about 5 centistokes.

The low viscosity siloxane polymer should be present in an amount sufficient to provide flowability to the composition to permit the composition to wet out, and to form a continuous even layer on a surface of a substrate. This amount will be dependent in part on the viscosities of the other components in the composition. Typically, the low viscosity siloxane polymer will be present at a total weight of about 40 weight % to about 80 weight %, more preferably from about 60 weight % to about 80 weight %, based on the total weight of the composition.

Non-limiting examples of siloxanes useful as the high viscosity siloxane polymer having a viscosity greater than about 1,000 centistokes include DC-360 12,500 ctsk polydimethylsiloxane, commercially available from Dow Corning of Midland, Mich.

The high viscosity siloxane polymer is typically present in the composition at a total weight of about 5 weight % to about 20 weight %, more preferably from about 5 weight % to about 15 weight %, based on the total weight of the composition.

The low viscosity siloxane polymer and the high viscosity siloxane polymer are combined with a reactive silicone polymer. The reactive silicone polymer is capable of radical induced polymerization, and therefore includes a crosslinkable group which is capable of undergoing a free-radical crosslinking reaction. Suitable crosslinkable groups include, but are not limited to, polymerizable ethylenically unsaturated moieties, in particular pendant ethylenically unsaturated groups, especially those that can be polymerized by means of a free-radical mechanism, examples of which are substituted and unsubstituted acrylates, methacrylates, alkenes and acrylamides. Polymerizable groups that are polymerized by a cationic mechanism, e.g., vinyl ether, epoxy and alkoxysilane groups, may also be employed, but are less preferred since a free-radical mechanism is typically easier to employ in such systems than a cationic mechanism.

The free-radical polymerization of the reactive silicone polymer is desirably initiated through exposure to radiation. As such, the reactive silicone polymer is desirably an acrylate or methacrylate functional silicone, which is crosslinkable upon exposure to ultraviolet (UV) light. For example, the reactive silicone polymer may be defined by the following structure:

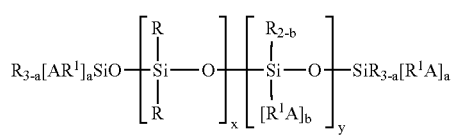

where R is selected from the group consisting of $C_{1-20}$ alkyl, aryl, cycloalkyl, aralkyl, and mixtures thereof; $R^1$ may or may not be present and if present is a divalent linking group comprising $C_{1-20}$ alkylene, hydroxy-functional alkylene, oxyalkylene, hydroxy-functional oxyalkylene, polyoxyalkylene, hydroxy-functional polyoxyalkylene, and mixtures thereof; A is an acrylic or methacrylic terminal group; each a is 0, 1, 2, or 3 and b is 0 or 1, provided that both a and b cannot be 0; x is an integer from 0 to about 1500; and y is an integer from about 1 to about 1500. Combinations and mixtures of reactive silicones may also be used.

As used herein, "-alkylene" refers to a divalent acyclic or cyclic saturated hydrocarbon alkanediyl group having a carbon chain length of from about 1 to about 20 carbons.

Acrylate-functional polydimethylsiloxanes are particularly desirable, examples of which are defined by the following structures:

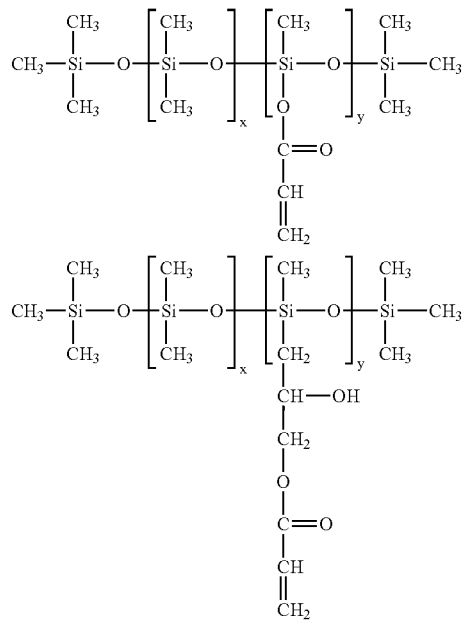

where the ratio of "methyl" siloxane to "acrylate" siloxane (x/y) is desirably from about 10 to 1 to about 60 to 1, desirably about 40 to 1.

Non-limiting examples of reactive silicones include SILCOLEASE PC-900, PC-910, PC-911 and PC-970, all of which are commercially available from Rhodia Inc. of Rocky Hill, S.C., and TEGO Rad 2700 commercially available from Goldschmidt Chemical Corp. of Hopewell, Va.

The reactive silicone should be present in an amount sufficient to provide the coating composition with a desired crosslinked matrix upon exposure to radiation that is sufficient to retain the coating composition on a desired substrate with appropriate lubricity. Typically, the reactive silicone will be present at a total weight of about 5 weight % to about 40 weight %, more preferably from about 20 weight % to about 30 weight %, based on the total weight of the composition.

In order to facilitate radical polymerization and/or to promote crosslinking of the reactive silicone polymer, the composition also includes a polymerization initiator to effect reaction of the ethylenically unsaturated group. Since, the reactive silicone polymer is desirably crosslinkable upon exposure to light, the initiator may comprise a photoinitiator. The photoinitiator should be capable of promoting free radical crosslinking of the ethylenically unsaturated component on exposure to light of a suitable wavelength and intensity, such as UV light. Any suitable photoinitiator may be used which is capable of initiating polymerization of the reactive silicone polymer upon exposure to UV light. Non-limiting examples of useful UV light-induced polymerization photoinitiators include ketones such as benzyl and benzoin, and acyloins and acyloin ethers. Alpha-hydroxy ketones are particularly desirable as photoinitiators for the compositions of the present invention. Non-limiting examples of commercially available products include IRGACURE 184 (1-hydroxycyclohexyl phenyl ketone), IRGACURE 907 (2-methyl-1-[4-(methylthio)phenyl]-2-morpholine propan-1-one), IRGACURE 369 (2-benzyl-2-N,N-dimethylamino-1-(4-morpholinophenyl)-1-butanone), IRGACURE 500 (the combination of 50% 1-hydroxy cyclohexyl phenyl ketone and 50% benzophenone), IRGACURE 651 (2,2-dimethoxy-1,2-diphenylethan-1-one), IRGACURE 1700 (the combination of 25% bis(2,6-dimethoxybenzoyl-2,4-, 4-trimethyl pentyl) phosphine oxide and 75% 2-hydroxy-2-methyl-1-phenyl-propan-1-one), DAROCUR 1173 (2-hydroxy-2-methyl-1-phenyl-propan-1-one), and DAROCUR 4265 (the combination of 50% 2,4,6-trimethylbenzoyldiphenyl-phosphine oxide and 50% 2-hydroxy-2-methyl-1-phenyl-propan-1-one), all of which are available from CIBA Corp., Tarrytown, N.Y.; and SARCURE SR-1121 (2-hydroxy-2-methyl-1-phenyl propanone) and ESACURE KIP-100F (a mixture of polymeric photoinitiators in 2-hydroxy-2-methyl-1-phenyl-propan-1-one), both of which are commercially available from Sartomer, Inc. of Exton, Pa. Of course, mixtures of different photoinitiators may also be used.

The photoinitiator is desirably in a liquid form to ensure appropriate mixing and distribution within the composition, although solid photoinitiators may also be used, provided that they are soluble in silicone to provide the composition as a homogeneous fluid. The photoinitiator should be present in an amount sufficient to provide the desired rate of photopolymerization. This amount will be dependent in part on the light source and the extinction coefficient of the photoinitiator. Typically, the photoinitiator components will be present at a total weight of about 0.01 to about 10%, more preferably from about 0.1 to about 5%, based on the total weight of the composition.

The film-forming compositions of the present invention may further include other additives, such as crosslinking agents, adhesion promoters, coupling agents, dyes and pigments, provided that such additives do not adversely affect the properties of the composition.

The film-forming composition may also optionally include a crosslinking agent for promoting crosslinking of the siloxane composition. Any crosslinking agent capable of promoting crosslinking may be embodied within the composition. Desirably, the crosslinking agent is an acrylate or a methacrylate crosslinking agent. For example, the crosslinking agent may be gamma-methylacryloxypropyl-trimethoxysilane, which is particularly desirable. A non-limiting example of a commercial product is gamma-methylacryloxypropyl-trimethoxysilane commercially available from Sigma of St. Louis, Mo.

When used, the crosslinking agent should be present in an amount sufficient to promote crosslinking of the composition upon exposure to radiation or after exposure to radiation. Typically, the crosslinking agent will be present at a total weight of about 0.01 to about 10%, more preferably from about 0.1 to about 5%, based on the total weight of the composition.

The film-forming compositions of the present invention are particularly useful for application on substrates such as medical devices. The compositions provide excellent lubricity, in particular, to polymeric substrates such as catheters. It is noted that the compositions are also particularly useful for application to metallic substrates, such as hypodermic needles and canals which are commonly manufactured from stainless steel. In such applications, the compositions of the present invention may include an adhesion promoter for promoting adhesion to the metallic substrate.

In particular, the compositions of the present invention may further include an amino-modified siloxane polymer as an adhesion promoter. This additional siloxane polymer is different than the low viscosity siloxane polymer and the high viscosity siloxane polymer, in that it includes amino functionality. Such amino-functional siloxane polymers provide for adhesion of the coating compositions of the present invention to metallic substrates, such as stainless steel hypodermic needles. Desirably, the adhesion promoter is an amino-containing polyorganosiloxane which includes at least one amino-functional group per molecule. More desirably, the adhesion promoter is an amino-functional dimethylsiloxane, such as an aminopropyl dimethylsiloxane copolymer or an aminoethylaminopropyl dimethylsiloxane copolymer. A non-limiting example of a commercially available product for this application is PS811 ((aminopropyl) methyl polydimethylsiloxane copolymer) commercially available from United Chemical Technologies, Inc. of Bristol, Pa.

The viscosity of the amino-modified siloxane polymer may be from about 5,000 centistokes to about 20,000 centistokes, desirably from about 10,000 centistokes to about 15,000 centistokes. When present, the amino-modified siloxane polymer should be present in an amount sufficient to promote adhesion of the composition to a metallic substrate. Typically, the amino-modified siloxane polymer will be present at a total weight of about 0.01 to about 10%, more preferably from about 0.1 to about 5%, based on the total weight of the composition.

The adhesion promoter (such as an amino-functional siloxane polymer) may also be used in a precoating layer or precoat. A precoat amino-functional siloxane composition will contain the amino-functional siloxane polymer in a solvent at a weight of about 0.01 to about 10%, more desirably about 0.1 to about 5%. Suitable solvents for the precoat composition include short chain hydrocarbons such as heptanes or octanes or mixtures thereof. In use, the precoat composition is applied to substrates such as needles or catheters by dip-coating for about one to ten seconds followed by drying to evaporate the solvent. A film forming composition of the present invention is then coated onto the precoat.

The adhesion promoter may be present in the film forming composition or in the precoat or in both. As such, the lubricious coating of the present invention may include only the film forming composition or the lubricious coating may include a first layer (an undercoat) of the precoat overlaid by the film forming composition.

As noted, the film-forming compositions with or without the precoating layer of the present invention are particularly useful for providing lubricity to substrates, and in particular to medical devices such as polymeric catheters and hypodermic needles for transdermal insertion. Accordingly, the compositions of the present invention may be applied to the desired substrate by contacting the surface of the medical device with the composition in liquid form. This contacting may be achieved in any known manner. For example, the coating composition may be applied to the substrate through dip-coating, spray coating, cascade-type application, application through absorbent pads, and the like. It is noted, however, that the compositions of the present invention are sufficiently flowable and liquid in and of themselves, and therefore do not require the use of any volatile organic solvents such as CFC's in order to deliver the siloxane coatings to the surface of the substrate. When a precoating layer is used, the precoat composition is applied to the surface of the substrate and dried to remove solvent. The film-forming composition is coated over the precoat.

It is noted that the compositions of the present invention are particularly well suited for spray coating applications to substrates such as needles and catheters. Spray coating of hollow substrates such as needle canals is particularly useful, in that a consistent thin coating can be evenly applied to the external surface, without compromising the internal lumen. For example, dip coating of such needle cannulas typically produces thicker coatings, and requires a procedure to remove any coating material from the internal lumen, such as by forcing air through the lumen during or after the coating procedure. Conventional organic solvent-based coating compositions, however, have not been particularly useful for spray coating applications. This is due at least in part to the difficulty in maintaining fluidity of the compositions as a result of evaporation of the solvent during the spraying procedure and premature curing of the composition from localized heating that may occur. The compositions of the present invention maintain fluidity until exposed to an appropriate source of radiation, such as UV light. As such, the curable compositions of the present invention are particularly useful for spray-type coating applications, in that they maintain their fluidity until cured through radiation.

In solvent-based lubricant systems, volatile organic solvents are used as a major component as a carrier for a very low concentration of silicone, such as about 3 percent by weight silicone within the volatile carrier liquid. Such a volatile carrier helps the silicone wet the surface and then evaporates, leaving behind a very thin film of silicone. With the compositions of the present invention, there is no volatile carrier solvent present, and therefore the silicone itself must wet the surface of the substrate. The compositions of the present invention typically have a higher viscosity than conventional silicone lubricants dissolved in a volatile carrier solvent for application. When the compositions of the present invention are coated onto a substrate, it is desirable to achieve a constant film thickness. In order to assist in maintaining the proper film thickness, the substrate surface may be subjected to vibration after coating with the composition of the present invention, which can assist in evenly distributing the coating composition on the substrate surface and removing any excess coating.

After application, the surface of the medical device including the coating thereon is exposed to radiation to promote curing and crosslinking of the composition. This may be accomplished by exposing the surface to a source of UV radiation. Various UV radiation light sources may be used, depending on the application. Desirably, the substrate is present on a moving surface which passes through a tunnel type oven including a UV light therein situated in a position to irradiate the surface of the substrate with UV light. Other curing methods include e-beam and gamma radiation. Subsequently, the coating may optionally be subjected to a further heat treatment in order to promote further curing/crosslinking of the composition.

Upon curing and crosslinking, the substrate is provided with a coating thereon which represents a reaction product of the composition as described above. The coating is sufficiently crosslinked to provide a stable coating evenly distributed on the surface of the substrate. Moreover, the coating is lubricious, and significantly reduces both the F2 peak penetration force and the F4 drag force for insertion of medical devices such as needles and catheters, when compared with conventional lubricious coatings.

The thickness of the coatings of the present invention is dependent upon the substrate surface and the application intended. The coating thickness should be sufficient to impart appropriate lubricity to the coating for the particular substrate. Desirably, the coating thickness is less than about 500 microns, more desirably less than about 200 microns, with coating thicknesses less than about 20 microns, more desirably less than about 5 microns, being particularly useful. Desirably, the coating weight is less than about 0.50 $mg/cm^2$, more desirably less than about 0.20 $mg/cm^2$.

Through the present invention, it has been discovered that excellent lubricious coatings can be formed from compositions which can be easily and effectively applied and coated onto medical device substrates without the need for volatile organic solvent carriers. It is believed that a synergism exists through the use of specific siloxane polymers which have similar chemical profiles and different reactivities, and which are diluted through the use of a low viscosity siloxane polymer. The low viscosity siloxane polymer is capable of diluting the organosilicone coating composition to a sufficient flowability without the need for such volatile solvents. Through the use of the low viscosity siloxane polymer, a homogeneous, clear, low viscosity film-forming composition is formed, which is capable of delivering the silicone coating composition to the substrate surface and maintaining the coating composition on the substrate surface until the coating is cured and/or crosslinked to form a final lubricious film which sufficiently adheres to itself and to the surface of the substrate and does not flow.

Upon curing, the reactive silicone forms a crosslinked network, which assists in binding the coating to the substrate surface and which acts as a reservoir for the silicone lubricant oil. In particular, the low viscosity and high viscosity silicone polymers which are not reacted with the reactive silicone remain uncured or only partially cured, thereby forming a silicone oil which is believed to be trapped within the crosslinked network of the cured reactive silicone. It is believed that the silicone oil is a mobile liquid which migrates to the surface, thereby providing lubricity to the surface while being effectively attached to the surface through the crosslinked network. Moreover, due to this trapping and migration effect, the silicone oil continually acts as a lubricant during use of the device. For example, during use, the silicone oil may be wiped away from the surface during contact of the surface with a patient's skin such as during insertion and penetration through the skin. While such contact may act to wipe away the lubricious coating, additional silicone oil trapped within the network can continuously migrate to the surface, thereby providing a continuous lubricious coating.

While the present invention is described in terms of a composition useful for IV catheters and medical needles, it is to be understood that the invention may be used on other medical devices where a lubricous surface on the device is desirable.

The invention will be more readily appreciated with reference to the following examples.

EXAMPLES

Example 1

Example 1 demonstrates a comparison of a catheter assembled with a coating composition according to the present invention which does not include any volatile organic solvent versus a comparative catheter coated with a conventional catheter lubricant coating composition including volatile organic solvent as a carrier medium.

In comparative Sample 1, a 20 gauge (ga) polyurethane catheter product was assembled by using a catheter tipping lubricant including an amino-functional silicone dissolved in a CFC-like volatile solvent for tipping the catheter to form a taper in known manner. A needle lubricant including a high viscosity polydimethyl siloxane dissolved in a CFC-like volatile solvent was then applied to the needle cannula by dip coating and allowing the solvent to evaporate before the catheter is placed over it. A catheter lubricant including a polydimethyl siloxane dissolved in a CFC-like volatile solvent was then applied over the entire finished product by dip coating and allowing the solvent to evaporate.

Separately, a catheter lubricant was prepared in accordance with the present invention as Sample 2, according to the following formulation:

TABLE 1

|  | Sample 2 |
|---|---|
| Acrylated silicone (%) (Goldschmidt Chemical TEGO Rad 2700) | 12.3 |
| 12,500 cstk polydimethyl siloxane (%) (Dow Corning DC-360) | 10.6 |
| Photoinitiator (%) (CIBA Darocur 1173) | 1.5 |
| 5 cstk polydimethyl siloxane (%) (United Chemical Technologies PS038) | 75.6 |

A 20 ga polyurethane IV catheter product was assembled as set forth above, but using a tipping lubricant and a needle lubricant including an amino-functional silicone diluted in a 100 centistoke polydimethylsiloxane, without the need for any evaporation of solvent after application. Following assembly, the catheter lubricant of Sample 2 was then applied over the entire finished product by spray the catheter lubricant over the entire outer surface of the catheter. The catheter with the lubricant applied thereto was then subjected to curing through exposure to a UV light oven cure system with a "D" type bulb with an exposure time of approximately 4 seconds.

The catheter products of Samples 1 and 2 were tested for penetration force and drag force using an Instron Series IX Automated Materials Testing System compression test through latex dental dam with a crosshead speed of 1 in/minute. The results are shown in Table 2.

TABLE 2

|  | Sample 1 (comparative) | | Sample 2 | |
|---|---|---|---|---|
|  | Force (g) | Normalized | Force (g) | Normalized |
| Needle Tip | 15 | 1.00 | 12.1 | 0.81 |
| Catheter Tip | 11.2 | 1.00 | 9.7 | 0.87 |
| Catheter Drag | 3.4 | 1.00 | 1.7 | 0.50 |

As is seen from a comparison of the results of Table 2, the penetration forces and the drag force for the catheter product including the UV cured lubricant (Sample 2) were substantially reduced from those of the catheter product including the conventional solvent-based lubricant (comparative Sample 1). When normalized for the conventional solvent-based lubricant, the inventive UV cured lubricant exhibits penetration forces between 81-87% of that of conventional lubricants, and exhibits a drag force of half the drag force exhibited by conventional lubricants.

Example 2

Example 2 demonstrates a comparison of Teflon catheters coated with a coating composition according to the present invention which does not include any volatile organic solvents as compared with a conventional solvent-based coating.

In comparative Sample 3, a set of fifteen (15) 22 gauge Teflon catheters (Angiocath Autoguard) were tapered by using a catheter tipping lubricant including a water-based silicone for tipping the catheters to form a taper in known manner. A solvent-based needle lubricant as set forth in Sample 1 above was used for assembly of the catheters. A solvent-based catheter lubricant as set forth in Sample 1 above was then applied over each of the assembled catheter products by dip coating and allowing the solvent to evaporate.

Separately, a catheter lubricant according to the present invention was prepared as Sample 4 according to the formulation in Table 3:

TABLE 3

|  | Sample 4 |
|---|---|
| Acrylated silicone (%) (Rhodia Silcolease PC-970) | 12.3 |
| 12,500 cstk polydimethyl siloxane (%) (Dow Corning DC-360) | 10.6 |
| Photoinitiator (%) (CIBA Darocur 1173) | 1.5 |
| 5 cstk polydimethyl siloxane (%) (United Chemical Technologies PS038) | 75.6 |

A set of fourteen (14) 22 gauge Teflon IV catheter products (Angiocath Autoguard) were assembled with a water based-tipping lubricant, and with a needle lubricant including an amino-functional silicone diluted in a 100 centistoke polydimethylsiloxane, without the need for any evaporation of solvent. Following assembly, the catheter lubricant of Sample 4 was then applied over each of the assembled catheters by spray coating the catheter lubricant over the entire outer surface of the catheters. The catheters with the lubricant applied thereto were then subjected to curing through exposure to UV light by passing through a Fusion UV oven cure system with an "D" type bulb with an exposure time of approximately 4 seconds.

The catheter products of Samples 3 and 4 were tested for penetration force and drag force as in Example 1 through latex and through a synthetic leather material, with the forces shown in Table 4.

TABLE 4

| | Sample 3 (comparative) | | | | Sample 4 | | | |
|---|---|---|---|---|---|---|---|---|
| | Latex | | Synthetic Leather | | Latex | | Synthetic Leather | |
| | Average Force (g) | Normalized | Average Force (g) | Normalized | Average Force (g) | Normalized | Average Force (g) | Normalized |
| Needle Tip | 13.3 [1.3] | 1.00 | 42.2 [5.6] | 1.00 | 10.6 [1.3] | 0.79 | 39.4 [9.4] | 0.93 |
| Catheter Tip | 19.50 [1.88] | 1.00 | 181.85 [30.89] | 1.00 | 12.2 [1.3] | 0.63 | 125.81 [26.54] | 0.69 |
| Catheter Average Drag | 4.0 [0.4] | 1.00 | 54.8 [13.3] | 1.00 | 3.3 [0.7] | 0.82 | 38.7 [8.0] | 0.71 |

[standard deviation]

As is seen from a comparison of the results of Table 4, the penetration forces and the drag forces for the catheter products including the UV cured lubricant (Sample 4) were substantially reduced from those of the catheter products including the conventional solvent-based lubricant (comparative Sample 3). When normalized for the conventional solvent-based lubricant, the inventive UV cured lubricant exhibits penetration and drag forces between 60-93% of that of conventional lubricants.

Example 3

Example 3 represents a comparative example demonstrating a stainless steel needle cannula with a conventional volatile organic solvent-based needle lubricant, according to the following composition in Table 4:

TABLE 5

| | Sample 5 (comparative) |
|---|---|
| Partially cured organosiloxane copolymer, polydimethylsiloxane, | 3.8 |

TABLE 5-continued

| | Sample 5 (comparative) |
|---|---|
| and amino-containing silicone polymer (%) | |
| CFC-like volatile solvent (%) | 96.2 |

A 22 gauge H1000 stainless steel needle cannula was coated with the composition of comparative Sample 5 by dip-coating, and the solvent was evaporated. Peak penetration force (F2) and drag force (F4) were measured, with the results used for normalized comparison in Example 4.

Example 4

Example 4 demonstrates film-forming compositions prepared in accordance with the present invention useful as needle lubricants, which do not include any volatile organic solvents. The following compositions were prepared according to Table 6:

TABLE 6

| | Sample No. | | | | | | | | |
|---|---|---|---|---|---|---|---|---|---|
| | 6 | 7 | 8 | 9 | 10 | 11 | 12 | 13 | 14 |
| Acrylated silicone (%) (Goldschmidt Chemical TEGO Rad 2700) | 11.8 | 25.4 | 25.4 | 25.5 | 25.0 | 24.8 | — | — | — |
| Acrylated silicone (%) (Rhodia Silcolease PC-970) | — | — | — | — | — | — | 25.0 | — | 25.0 |
| Acrylated silicone (%) (Rhodia Rhodorsil 21621) | — | — | — | — | — | — | — | 25.0 | — |
| Photoinitiator (%) (Ciba Irgacure 1700) | — | 1.6 | — | — | — | — | — | — | — |
| Photoinitiator (%) (Ciba Darocur 1173) | 0.4 | — | 1.6 | 4.6 | 3.2 | 1.6 | 2.5 | 2.5 | 2.5 |
| Crosslinking agent (%) (γ-methylacryloxypropyltrimethoxysilane, Sigma M6514) | 0.4 | 0.4 | 0.4 | — | — | — | — | — | — |
| 12,500 cstk polydimethyl siloxane (%) (Dow Corning DC-360) | 12.1 | 6.2 | 6.4 | 6.2 | 6.3 | 6.3 | 6.0 | 6.0 | — |
| 350 cstk polydimethyl siloxane (%) (Dow Corning DC-360) | — | — | — | — | — | — | — | — | 71.7 |
| Amino-functional silicone (%) (United Chemical Technologies PS811) | 0.4 | 0.8 | 0.8 | 0.8 | 0.8 | — | 0.8 | 0.8 | 0.8 |
| 5 cstk polydimethyl siloxane (%) (United Chemical Technologies PS038) | 74.9 | 65.5 | 65.4 | 65.9 | 64.6 | 67.3 | 65.7 | 65.7 | — |

A series of 22 gauge H1000 stainless steel needle cannulae were independently coated with the compositions of Samples 6-11 by dip-coating and Sample 12 by spray coating. Samples 13 and 14 were not further evaluated as coatings, as Sample 13 was phase separated and Sample 14 resulted in a gel. The thus coated needles were then subjected to curing through exposure to UV light by passing the needles bevel side up through a Fusion UV tunnel type oven cure system with a "D" type bulb situated above the product, at various belt speeds of 11 feet/minute, 4 feet/minute and 0.5 feet/minute. Sample 10 was subjected to dual curing by successively passing the coated needle through the cure oven twice at line speeds of 4 feet/minute and 0.5 feet/minute, and Sample 12 was passed through the oven 4 times at a line speed of 3 feet/minute.

The needles coated with the compositions of Samples 6-12 were then tested for peak penetration force (F2) and drag force (F4). In the testing procedure, each needle is driven substantially vertically downward into a standard commercial vial stopper at a substantially constant rate of about 1.25 centimeters/second using an instrument with the needle being tested affixed to a calibrated load cell. All of the needles used were 22 gauge and about 3.8 centimeters long, however, the coatings and methods of the invention are applicable to and include other sizes of needles that may be required in any procedure where a lubricant is beneficial. The initial force begins as the distal point of the needle touches the substrate (i.e. the patient's skin or in this case a rubber stopper), stretches the substrate and shows an increasing resistance force until the distal point of the needle begins to cut the substrate. This peak penetration force is termed "F2". As soon as the point begins to cut through the substrate, the recorded force decreases until the elongate tube is introduced through the cut initiated by the point. Once only the tube is moving through the cut, the observed force is termed the drag force or "F4". Lubrication of a hypodermic needle reduced both the F2 and F4 forces dramatically. The results were normalized against the peak penetration force (F2) and drag force (F4) of the coated needle of Sample 5 in Example 3, with the normalized results shown in Table 7.

TABLE 7

| | Sample No. | | | | | | |
|---|---|---|---|---|---|---|---|
| | 6 | 7 | 8 | 9 | 10 | 11 | 12 |
| F2 Penetration Forces (g) | | | | | | | |
| @ 11 ft/min cure speed | 1.78 | 1.35 | 1.16 | 1.2 | NM* | 2.08 | NM* |
| @ 4 ft/min cure speed | 1.51 | 1.55 | 1.69 | 1.79 | 1.66 | 2.02 | NM* |
| @ 3 ft/min cure speed (4×) | NM* | NM* | NM* | NM* | NM* | NM* | 1.05 |
| @ 0.5 ft/min cure speed | 1.05 | 0.83 | 0.84 | 0.83 | 0.85 | 0.93 | NM* |
| @ 0.5 ft/min cure speed (2×) | NM* | NM* | NM* | 0.84 | NM* | NM* | NM* |
| F4 Drag Forces (g) | | | | | | | |
| @ 11 ft/min cure speed | 0.29 | 0.27 | 0.31 | 0.31 | NM* | 0.76 | NM* |
| @ 4 ft/min cure speed | 0.27 | 0.30 | 0.34 | 0.35 | 0.29 | 0.79 | NM* |
| @ 3 ft/min cure speed (4×) | NM* | NM* | NM* | NM* | NM* | NM* | 0.28 |
| @ 0.5 ft/min cure speed | 0.32 | 0.40 | 0.26 | 0.28 | 0.29 | 0.98 | NM* |
| @ 0.5 ft/min cure speed (2×) | NM* | NM* | NM* | 0.32 | NM* | NM* | NM* |

*NM - Not Measured

As is seen through the results of Table 7, the drag force for the needles including the UV cured lubricant were excellent, and were substantially reduced from those of the needle including a conventional solvent-based lubricant. In particular, when normalized for the conventional solvent-based lubricant, each of the lubricants of the present invention which included an amino-functional siloxane as an adhesion promoter demonstrated drag forces that were 26-35% of the drag force of the comparative solvent-based needle lubricant at all cure speeds. Even the lubricant which did not include any adhesion promoter (Sample 11) achieved a drag force less than the comparative solvent-based lubricant. Moreover, the penetration forces for needles coated with the inventive lubricants were acceptable, and the penetration forces were significantly improved for needles coated with each of the inventive compositions and cured at line speeds of 0.5 feet/minute.

Example 5

Example 5 demonstrates that film-forming compositions prepared in accordance with the present invention are also useful as needle lubricants when used with a precoat of an amino-functional siloxane polymer.

A series of 22 gauge H1000 stainless steel needle cannulae (Series A) were independently coated with the composition of Sample 12 by dip-coating. Two additional series of 22 gauge H1000 stainless steel needle cannulae were precoated in a 1 wt. % solution of an amino-functional silicone (United Chemical Technologies PS 811) in a $C_7$-$C_8$ hydrocarbon solvent (Chevron Phillips Chemical Soltrol® 10). Series B was dipped in the amino-functional silicone solution for one second. Series C was dipped in the solution for ten seconds. After drying, the Series B and Series C needles were coated with the composition of Sample 12 by dip-coating.

The needles of Series A, B and C were then subjected to curing through exposure to UV light by passing the needles flat through a Honle ACM UV cure system for 9 seconds with an "H" type bulb situated above the product, at a belt speed of 5 feet/minute.

The needles of Series A, B and C were then tested for peak penetration force (F2) and drag force (F4) using the testing procedure of Example 4 in multiple penetration of vial stoppers with the results shown in Table 8.

TABLE 8

| | Series A (no precoat) | Series B (1 sec precoat) | Series C (10 sec precoat) |
|---|---|---|---|
| F2 Penetration Forces (g) | | | |
| Vial stopper 1st penetration | 223 | 196 | 200 |
| Vial stopper 2nd penetration | 267 | 220 | 219 |
| Vial stopper 3rd penetration | 290 | 240 | 230 |
| Vial stopper 4th penetration | 328 | 259 | 237 |

TABLE 8-continued

| | Series A (no precoat) | Series B (1 sec precoat) | Series C (10 sec precoat) |
|---|---|---|---|
| F4 Drag Forces (g) | | | |
| Vial stopper 1st penetration | 21 | 20 | 18 |
| Vial stopper 2nd penetration | 23 | 23 | 23 |
| Vial stopper 3rd penetration | 23 | 26 | 24 |
| Vial stopper 4th penetration | 23 | 26 | 24 |

As is seen through the results of Table 8, the penetration force for the needles including the UV cured lubricant with an amino-functional silicone precoat were substantially reduced from those of the needles having the UV cured lubricant. In particular, the needles of Series B (one second precoat dip) exhibited about 12-21% reduction in penetration force from the forces of the Series A needles with no precoat. The needles of Series C (ten second precoat dip) exhibited about 10-28% reduction in penetration force. It also expected that similar results to those reported for Series B and C are achievable using the precoat with a film forming composition that does not include the adhesion promoter.

Although illustrative embodiments of the present invention have been described herein with reference to the examples, it is to be understood that the invention is not limited to those precise embodiments, and that various other changes and modifications may be effected therein by one skilled in the art without departing from the scope or spirit of the invention.

What is claimed is:

1. A film-forming composition comprising:
a first siloxane polymer having a viscosity of less than about 50 centistokes;
a second siloxane polymer having a viscosity of greater than about 1,000 centistokes;
a reactive silicone polymer capable of crosslinking upon exposure to radiation;
a photoinitiator for promoting crosslinking of the reactive silicone polymer upon exposure to radiation; and
a third siloxane polymer having amino functionality.

2. A film-forming composition as in claim 1, wherein the first siloxane polymer and the second siloxane polymer are independently selected from compounds defined by the formula:

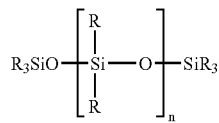

wherein R is selected from the group consisting of alkyl $C_{1-20}$, haloalkyl, aryl, haloaryl, cycloalkyl, aralkyl, and mixtures thereof, and n is an integer from about 3 to about 1500.

3. A film-forming composition as in claim 2, wherein the first siloxane polymer is a polydimethylsiloxane having a molecular weight of from about 400 to about 1300.

4. A film-forming composition as in claim 3, wherein the first siloxane polymer has a viscosity of from about 2 to about 10 centistokes.

5. A film-forming composition as in claim 2, wherein the second siloxane polymer is a polydimethylsiloxane having a molecular weight of from about 60,000 to about 70,000.

6. A film-forming composition as in claim 5, wherein the second siloxane polymer has a viscosity of from about 10,000 to about 15,000 centistokes.

7. A film-forming composition as in claim 1, wherein the reactive silicone polymer is capable of crosslinking upon exposure to ultraviolet light.

8. A film-forming composition as in claim 1, wherein the reactive silicone polymer is a silicone acrylate.

9. A film-forming composition as in claim 8, wherein the reactive silicone polymer is defined by the structure:

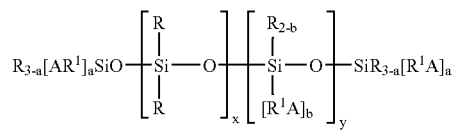

wherein R is selected from the group consisting of $C_{1-20}$ alkyl, aryl, cycloalkyl, aralkyl, and mixtures thereof; $R^1$ may or may not be present and if present is a divalent linking group comprising $C_{1-20}$ alkylene, hydroxy-functional alkylene, oxyalkylene, hydroxy-functional oxyalkylene, polyoxyalkylene, hydroxy-functional polyoxyalkylene, and mixtures thereof; A is an acrylic or methacrylic terminal group; each a is 0, 1, 2, or 3 and b is 0 or 1, provided that both a and b cannot be 0; x is an integer from 0 to about 1500; and y is an integer from about 1 to about 1500.

10. A film-forming composition as in claim 1, wherein the photoinitiator is an alpha-hydroxy ketone.

11. A film-forming composition as in claim 1, further comprising a crosslinking agent.

12. A film-forming composition as in claim 11, wherein the crosslinking agent is gamma-methylacryloxypropyl-trimethoxysilane.

13. A film-forming composition as in claim 1, further comprising an adhesion promoter for promoting adhesion to a substrate surface.

14. A film-forming composition as in claim 1, wherein the third siloxane polymer is an aminopropyl dimethylsiloxane copolymer.

15. A medical device comprising a metal surface having a lubricious coating thereon, said lubricious coating comprising the reaction product of claim 14.

16. A medical device comprising a polymeric surface having a lubricious coating thereon, said lubricious coating comprising the reaction product of claim 1.

17. A lubricious coating comprising:
a first layer comprising an adhesion promoter; and
a second layer comprising the film-forming composition including,
a first siloxane polymer having a viscosity of less than about 50 centistokes;
a second siloxane polymer having a viscosity of greater than about 1,000 centistokes;
a reactive silicone polymer capable of crosslinking upon exposure to radiation; and
a photoinitiator for promoting crosslinking of the reactive silicone polymer upon exposure to radiation;
wherein the adhesive promoter promotes adhesion of the film-forming composition to a substrate surface.

18. A lubricious coating as in claim 17, wherein the adhesion promoter comprises an amino-functional siloxane polymer.

19. A lubricious coating as in claim 17, wherein the adhesion promoter comprises an aminopropyl dimethylsiloxane copolymer.

20. A lubricious coating as in claim 17, wherein the film-forming composition further comprises an adhesion promoter for promoting adhesion of the film-forming composition to a substrate surface.

21. A lubricious coating as in claim 20, wherein the adhesion promoter in the film-forming composition comprises an amino-functional siloxane polymer.

22. A lubricious coating as in claim 20, wherein the adhesion promoter in the film-forming composition comprises an aminopropyl dimethylsiloxane copolymer.

23. A film-forming composition comprising:
  a) from about 40 weight % to about 80 weight %, based on the total weight of the composition, of a first polyalkylsiloxane having a viscosity of less than about 50 centistokes;
  b) from about 5 weight % to about 20 weight %, based on the total weight of the composition, of a second polyalkylsiloxane having a viscosity of greater than about 1,000 centistokes;
  c) from about 5 weight % to about 40 weight %, based on the total weight of the composition, of a reactive silicone polymer capable of crosslinking upon exposure to radiation;
  d) from about 0.5 weight % to about 10 weight %, based on the total weight of the composition, of a photoinitiator for promoting crosslinking of the reactive silicone polymer upon exposure to radiation; and
  e) optionally, from about 0.1 weight % to about 5 weight %, based on the total weight of the composition, of a crosslinking agent.

24. A film-forming composition as in claim 23, wherein the first siloxane polymer and the second siloxane polymer are independently selected from compounds defined by the structure:

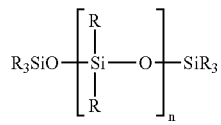

wherein R is selected from the group consisting of alkyl $C_{1-20}$, haloalkyl, aryl, haloaryl, cycloalkyl, aralkyl, and mixtures thereof, and n is an integer from about 3 to about 1500.

25. A film-forming composition as in claim 23, wherein the reactive silicone polymer is a silicone acrylate.

26. A film-forming composition as in claim 25, wherein the reactive silicone polymer is defined by the structure:

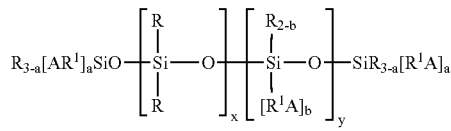

wherein R is selected from the group consisting of $C_{1-20}$ alkyl, aryl, cycloalkyl, aralkyl, and mixtures thereof; $R^1$ may or may not be present and if present is a divalent linking group comprising $C_{1-20}$ alkylene, hydroxy-functional alkylene, oxyalkylene, hydroxy-functional oxyalkylene, polyoxyalkylene, hydroxy-functional polyoxyalkylene, and mixtures thereof; A is an acrylic or methacrylic terminal group; each a is 0, 1, 2, or 3 and b is 0 or 1, provided that both a and b cannot be 0; x is an integer from 0 to about 1400; and y is an integer from about 1 to about 1500.

27. A film-forming composition as in claim 23, further comprising a third siloxane polymer having amino functionality.

28. A film-forming composition as in claim 27, wherein the third siloxane polymer is an aminopropyl dimethylsiloxane copolymer.

29. A medical device coated with a lubricious coating, said lubricious coating comprising the reaction product of:
  a first siloxane polymer having a viscosity of less than about 50 centistokes;
  a second siloxane polymer having a viscosity of greater than about 1,000 centistokes;
  a reactive silicone polymer capable of crosslinking upon exposure to radiation; and
  a photoinitiator for promoting crosslinking of the reactive silicone polymer upon exposure to radiation;
  wherein said lubricious coating further includes an adhesion promoting layer coated on said device, said reaction product being coated on said adhesion promoting layer.

30. A medical device as in claim 29, wherein the medical device comprises a polymeric material.

31. A medical device as in claim 30, wherein the medical device comprises a catheter.

32. A medical device as in claim 29, wherein the lubricious coating further comprises a third siloxane polymer having amino functionality.

33. A medical device as in claim 32, wherein the medical device comprises a metallic material.

34. A medical device as in claim 33, wherein the medical device comprises a stainless steel needle cannula.

35. A medical device as in claim 29, wherein said adhesion promoting layer comprises an amino-functional siloxane polymer.

36. A medical device as in claim 29, wherein said adhesion promoting layer comprises an aminopropyl dimethylsiloxane copolymer.

37. A method for providing the surface of a medical device with a lubricous coating comprising:
  contacting the medical device with a liquid composition substantially free of volatile organic solvent comprising:
    a first siloxane polymer having a viscosity of less than about 50 centistokes;
    a second siloxane polymer having a viscosity of greater than about 1,000 centistokes;
    a reactive silicone polymer capable of crosslinking upon exposure to radiation; and
    a photoinitiator for promoting crosslinking of the reactive silicone polymer upon exposure to radiation; and
  distributing the liquid composition evenly on the surface by vibrating the surface;
  exposing the thus coated surface to radiation to promote curing of the composition.

38. A method as in claim 37, wherein the exposing step comprises exposing the surface to ultraviolet light.

39. A method for providing the surface of a medical device with a lubricous coating comprising:

coating the medical device with an adhesion promoting composition;

contacting the medical device with a liquid composition substantially free of volatile organic solvent comprising:
- a first siloxane polymer having a viscosity of less than about 50 centistokes;
- a second siloxane polymer having a viscosity of greater than about 1,000 centistokes;
- a reactive silicone polymer capable of crosslinking upon exposure to radiation; and
- a photoinitiator for promoting crosslinking of the reactive silicone polymer upon exposure to radiation; and exposing the thus coated surface to radiation to promote curing of the composition; such that the liquid composition is coated on the adhesion promoting composition.

40. A method as in claim 39, wherein the adhesion promoting composition comprises an amino-functional siloxane polymer.

41. A method as in claim 39, wherein the adhesive promoting composition comprises an aminopropyl dimethylsiloxane copolymer.

42. A lubricious coating for a polymeric substrate substantially free of volatile organic solvents consisting essentially of:
a) a first siloxane polymer having a viscosity of less than about 50 centistokes and defined by the following structure:

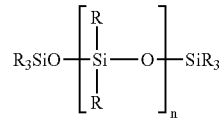

wherein R is selected from the group consisting of alkyl $C_{1-20}$, haloalkyl, aryl, haloaryl, cycloalkyl, aralkyl, and mixtures thereof, and n is an integer from about 3 to about 50;

b) a second siloxane polymer having a viscosity of greater than about 1,000 centistokes and defined by the following structure:

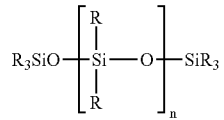

wherein R is selected from the group consisting of alkyl $C_{1-20}$, haloalkyl, aryl, haloaryl, cycloalkyl, aralkyl, and mixtures thereof, and n is an integer from about 350 to about 1380;

c) a reactive silicone polymer capable of crosslinking upon exposure to radiation and defined by the following structure:

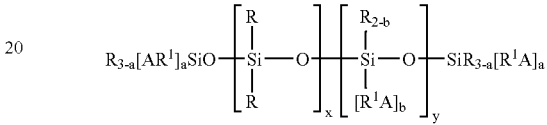

wherein R is selected from the group consisting of $C_{1-20}$ alkyl, aryl, cycloalkyl, aralkyl, and mixtures thereof, $R^1$ may or may not be present and if present is a divalent linking group comprising $C_{1-20}$ alkylene, hydroxy-functional alkylene, oxyalkylene, hydroxy-functional oxyalkylene, polyoxyalkylene, hydroxy-functional polyoxyalkylene, and mixtures thereof, A is an acrylic or methacrylic terminal group; each a is 0, 1, 2, or 3 and b is 0 or 1, provided that both a and b cannot be 0; x is an integer from 0 to about 1380; and y is an integer from about 1 to about 1500;

d) a photoinitiator for promoting crosslinking of the reactive silicone polymer upon exposure to radiation; and e) a polyorganosiloxane having amino functionality.

43. A coating as in claim 42, wherein the polyorganosiloxane having amino functionality comprises an aminopropyl dimethylsiloxane copolymer.

* * * * *